US011220507B2

(12) United States Patent
Beck et al.

(10) Patent No.: US 11,220,507 B2
(45) Date of Patent: Jan. 11, 2022

(54) PROCESS FOR THE PREPARATION OF RUCAPARIB AND NOVEL SYNTHESIS INTERMEDIATES

(71) Applicant: Advitech Advisory and Technologies SA, Lausanne (CH)

(72) Inventors: Brent Christopher Beck, Apex, NC (US); Joe B. Perales, Durham, NC (US); Jason D. Speake, Winston-Salem, NC (US); Ilaria Ferrando, Lugano (CH)

(73) Assignee: Advitech Advisory and Technologies SA, Lausanne (CH)

( * ) Notice: Subject to any disclaimer, the term of this patent is extended or adjusted under 35 U.S.C. 154(b) by 0 days.

(21) Appl. No.: 16/770,811

(22) PCT Filed: Dec. 15, 2017

(86) PCT No.: PCT/EP2017/083174
§ 371 (c)(1),
(2) Date: Jun. 8, 2020

(87) PCT Pub. No.: WO2019/115000
PCT Pub. Date: Jun. 20, 2019

(65) Prior Publication Data
US 2020/0331916 A1    Oct. 22, 2020

(51) Int. Cl.
| | | |
|---|---|---|
| *C07D 487/06* | (2006.01) |
| *C07D 209/14* | (2006.01) |
| *C07D 403/08* | (2006.01) |
| *C07D 209/32* | (2006.01) |
| *C07C 243/22* | (2006.01) |
| *C07D 487/04* | (2006.01) |
| *C07D 209/48* | (2006.01) |
| *C07D 403/06* | (2006.01) |

(52) U.S. Cl.
CPC .......... *C07D 487/04* (2013.01); *C07C 243/22* (2013.01); *C07D 209/48* (2013.01); *C07D 403/06* (2013.01); *C07B 2200/13* (2013.01)

(58) Field of Classification Search
CPC .. C07D 487/06; C07D 209/14; C07D 403/08; C07D 209/32; C07C 243/22
See application file for complete search history.

(56) References Cited

FOREIGN PATENT DOCUMENTS

| WO | 200042040 | 7/2000 |
| WO | 2006033003 | 3/2006 |
| WO | 2011/098971 | 8/2011 |

OTHER PUBLICATIONS

International Search Report issued by the EPO dated Mar. 13, 2018 for PCT/EP2017/083174.
Adam T. Gillmore et al: "Multkilogram Scale-Up of a Reductive Alkylati on Route to a Novel PARP Inhibitor", Organic Process Research and Development, vol. 16, No. 12, Dec. 21, 2012.
David L. Hughes: "Patent Review of Manufacturing Routes to Recently Approved PARP Inhibitors: Olaparib, Rucaparib, and Niraparib",Organic Process Research and Development, vol. 21, No. 9, Aug. 21, 2017.

*Primary Examiner* — Bruck Kifle
(74) *Attorney, Agent, or Firm* — Silvia Salvadori

(57) ABSTRACT

The present invention relates to a process for the preparation of rucaparib; the invention also refers to novel intermediates of synthesis as well as their use in the preparation of i.a. rucaparib.

13 Claims, 1 Drawing Sheet

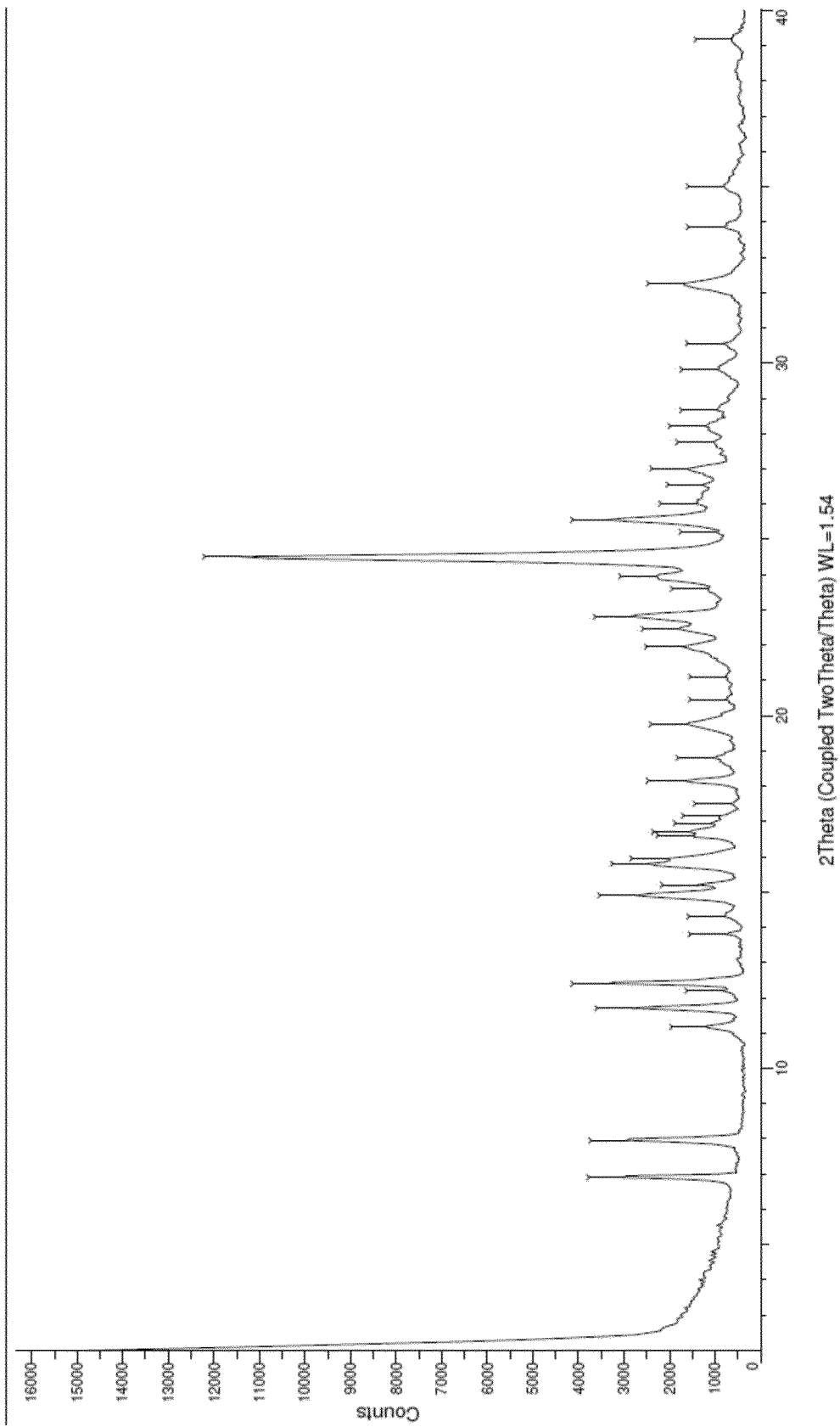

PROCESS FOR THE PREPARATION OF RUCAPARIB AND NOVEL SYNTHESIS INTERMEDIATES

This application is a U.S. national stage of PCT/EP2017/083174 filed on 15 Dec. 2017, the contents of which is incorporated herein by reference in its entirety.

TECHNICAL BACKGROUND

Rucaparib is the International Non-proprietary Name (INN) of 8-fluoro-2-{4-[(methylamino)methyl]phenyl}-1,3,4,5-tetrahydro-6H-pyrrolo[4,3,2-ef][2]benzazepin-6-one (as reported in WHO Drug Information Vol 26, No. 1, 2012), herein after referred to only as rucaparib, and has the following formula (I)

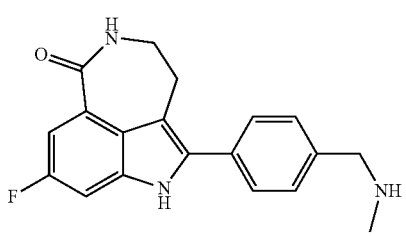

Rucaparib is a drug which was recently approved by the FDA for the treatment of ovarian cancer in patients with a deleterious BRCA-mutation and is still under clinical trials for investigating its potential activity for the treatment of other cancer diseases.

Some synthesis of rucaparib are known in the literature, as described for instance in WO2000/042040, in WO2006/033003 and in Organic Process Research & Development 2012, 16(1897). However, the routes of synthesis disclosed in the above documents involve 10 to 13 reaction steps, which is not valuable in industrial scale production.

There is therefore a need to provide alternative routes of synthesis for the preparation of rucaparib, which comprise less reaction steps and possibly afford better yields.

OBJECTS OF THE INVENTION

It is an object of the present invention to provide a new process for the preparation of rucaparib which is more compatible with the industrial scale production, involving less reaction steps with respect to the known processes.

It is a further object of the invention to provide novel intermediate compounds, as well as their use in the preparation of i.a. rucaparib.

BRIEF DESCRIPTION OF THE FIGURE

FIG. 1 shows the XRPD of rucaparib obtained according to Example 3.

DESCRIPTION OF THE INVENTION

Thus, according to one of its aspects, the present invention relates to a process for the preparation of rucaparib of formula (I)

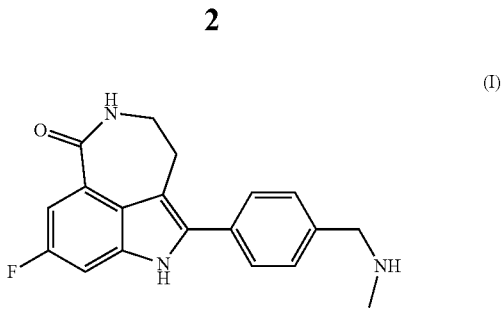

or one of its salts, which comprises:
a. reacting a compound of formula (II)

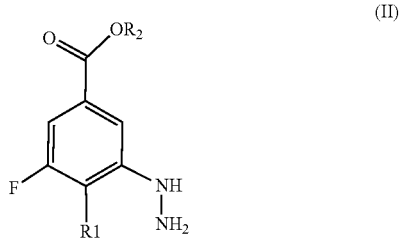

wherein
R1 is selected from hydrogen a halogen atom, a cyano group, a sulfonyl group, an —O-sulfonyl group; and
R2 is selected from hydrogen, an alkyl group, an aryl group or an aryl-alkylgroup; or one of its salts,
with a compound of formula (III)

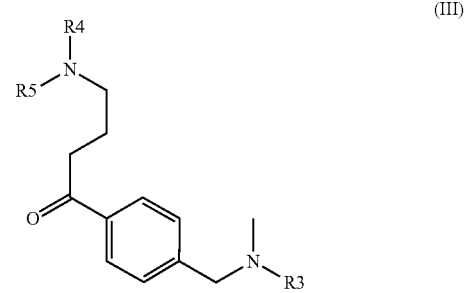

wherein R3 is a protecting group;
R4 is hydrogen or a protecting group; and
R5 is a protecting group;
or R4 and R5, together with the nitrogen atom to which they are bound, form a cyclic protecting group;
to obtain a compound of formula (IV)

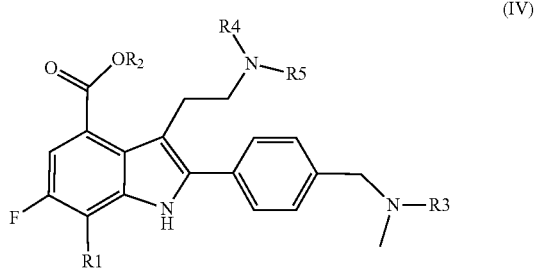

wherein R1, R2, R3, R4 and R5 are as above defined, b. converting compound (IV) into the corresponding lactam of formula (V)

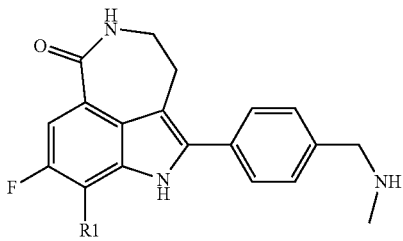

wherein R1 is as above defined:

c. when R1 is other than a hydrogen atom, removing R1 from the lactam of formula (V) to obtain rucaparib of formula (I);

d. optionally, transforming rucaparib in one of its salts.

The salts of rucaparib may be, according to the invention, either pharmaceutically acceptable or non-pharmaceutically acceptable salts. Non-pharmaceutically acceptable salts may be used, for example, in the isolation or purification of rucaparib. The salts may be any suitable salt and include salts with organic or inorganic acids or salts with organic or inorganic bases. According to a preferred embodiment, the salts rucaparib are pharmaceutically acceptable salts, such as, for instance, hydrochloride, phosphate, maleate, camsylate and the like.

The salts of compound of formula (II) may be any suitable salt and include salts with organic or inorganic acids such as hydrochloride, hydrobromide, phosphate, acetate, oxalate, and the like, salts, as well as, when R2 is a hydrogen atom, salts with organic or inorganic bases, such as salts with sodium, potassium, primary, secondary or tertiary amines, and the like. According to preferred embodiment, compound (II) is used in a salified form, preferably as its hydrochloride salt.

According to the present invention:

the expression "halogen atom" indicates a chlorine, bromine or iodine atom;

the expression "sulfonyl group" indicates a R'—S(=O)$_2$O— group, wherein R is selected from —OH, an optionally substituted alkyl group and an optionally substituted aryl, and includes an optionally substituted phenylsulfonyl group;

the expression "—O-sulfonyl group" indicates a R'—S(=O)$_2$—O— group, R' is selected from an an optionally substituted alkyl group and an optionally substituted aryl, and includes a triflate and a tosylate group;

the expression "alkyl group" indicates a linear or branched, saturated or non-saturated optionally substituted alkyl chain, such as for instance a $C_1$-$C_6$ alkyl, preferably selected from methyl, ethyl, n-propyl, iso-propyl and tert-butyl groups;

the expression "aryl group" indicates an optionally substituted aromatic groups, preferably phenyl or substituted phenyl groups;

the expression "aryl-alkyl group" indicates an optionally substituted aromatic group bound to the carboxylic group by an alkylene chain, preferably benzyl or substituted benzyl groups;

the expression "protecting group" indicates any protecting group suitable for the protection of the amino-group (as disclosed for instance in T. W. Greene, John Wiley & Sons, Ltd, *Protective Groups in Organic Synthesis*", 5$^{th}$ ed., 2014), and include acyl groups, such as optionally substituted acetyls for instance trifluoroacetyl or trichloroacetyl groups, sulfonyl groups, —O-sulfonyl groups as above defined or a carboxybenzyl group;

the expression "cyclic protecting group" indicates a succinimmide, a phthalimide and the like;

protecting groups R3, R4 and R5 may be equal or different.

According to a preferred embodiment, compound of formula (II) is in in the form of its hydrochloride salt;

R1 is a hydrogen atom or a halogen atom, preferably a bromine atom;

R2 is a hydrogen atom;

R3 is a substituted acyl, preferably a substituted acetyl, more preferably trifluoroacetyl or trichloroacetyl;

R4 and R5 together with the nitrogen atom to which they are bound, form a cyclic protecting group as above defined, preferably a phthalimide group.

According to a preferred embodiment, the process of the invention is as depicted in Scheme (I):

Scheme (I)

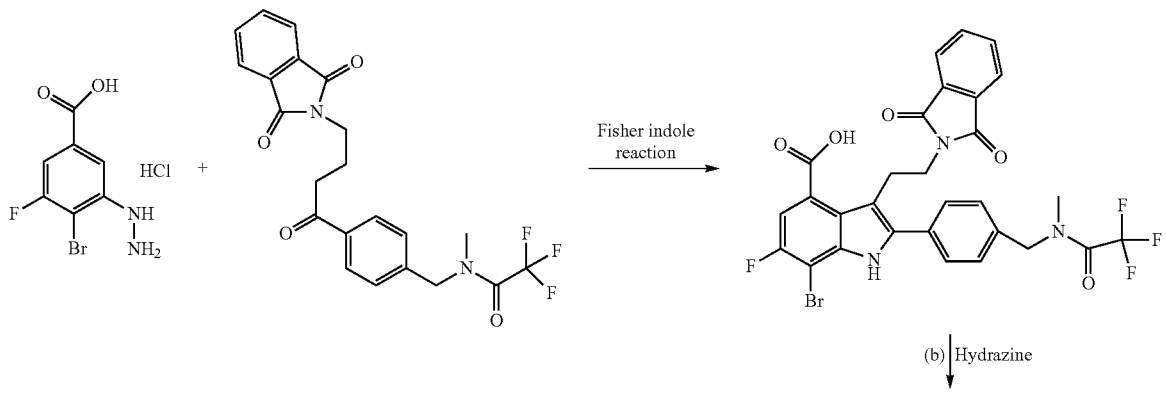

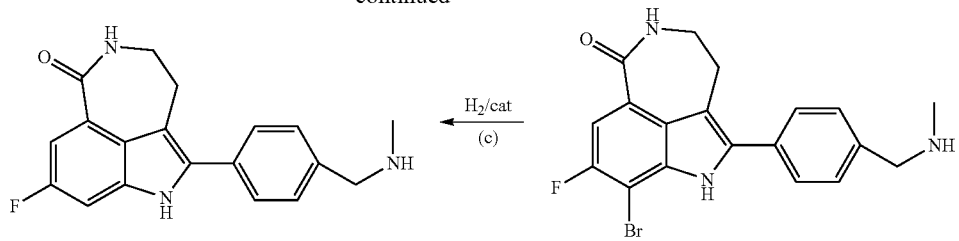

The Fisher indole reaction of step (a) may be carried out starting from compounds of formula (II) and (III) according to the methods known in the art. Typically, step (a) is carried out in the presence of an acid, preferably a weak acid such as for instance acetic acid, oxalic acid, phosphoric acid, and the like, or a Lewis acid, such boron trifluoride and the like, or mixtures thereof. Preferably, step (a) is carried out in the presence of acetic acid and boron trifluoride, advantageously glacial acetic acid and boron trifluoride diethyl etherate.

Step (a) is preferably carried out by heating the reaction mixture at a temperature from 40° C. to the reflux temperature, for instance for instance from 60° C. to the reflux temperature, preferably at about 90° C., advantageously in an inert atmosphere. Upon completion of the reaction, the compound of formula (IV) thus obtained may be isolated by known conventional work-up techniques and either purified or used as such in the subsequent reaction step.

Step (b) may be carried out in the presence of hydrazine in a suitable solvent or mixture of solvents, such as for instance alcohols and/or ethers, preferably in a mixture of ethanol and tetrahydrofuran. Other possible reagents may however be used in lieu of hydrazine such as, for instance, methylamine, phenylhydrazine, sodium sulfide ($Na_2S$), hydroxyl amine, and the like.

Step (b) is preferably carried out by heating the reaction mixture at a temperature from 40° C. to the reflux temperature, for instance from 80° C. to the reflux temperature, preferably up to about 110° C.

If necessary or desired, R4 and R5 may be removed before step (b) to form compound of formula (VI)

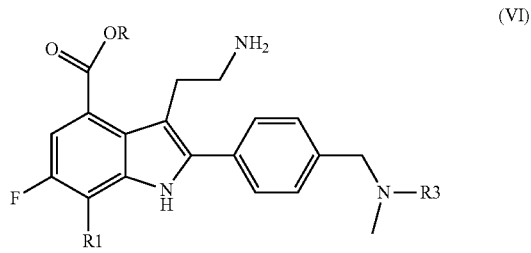

(VI)

or one of its salts, wherein R1, R2 and R3 are as above defined.

Alternatively, R4 and R5 are spontaneously removed in the reaction of step in which the lactam of formula (V) is formed.

When R1 is other than a hydrogen atom, it may be removed from compound of formula (V) according to the method known in the art. For instance, when R1 is a halogen atom such as a bromine atom, it may be removed by hydrogenation with $H_2$ in the presence of a solvent or a mixture of solvents, and of a catalyst for example and preferably, with $H_2$ and palladium in an alcohol, such as methanol.

Rucaparib as obtained in step (c) may be isolated and, if needed, purified according to any known method and, if necessary or desired, converted into a salt thereof; the skilled in the art is perfectly able to do.

Details of representative conditions useful to carry out the process of the invention are reported in the Experimental Section which follows.

The compound of formula (II) may be prepared according to the following Scheme (II):

Scheme (II)

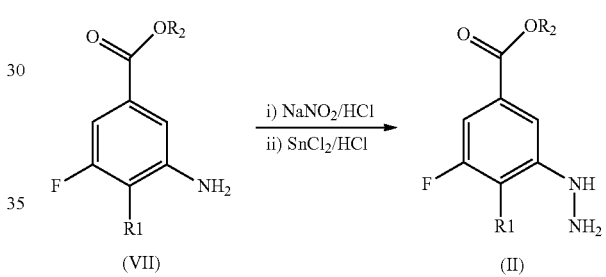

wherein R1 and R2 are as above defined.

The compound of formula (II) as well as its salts, is a novel compound and constitutes a further subject-matter of the present invention.

The compound of formula (III) may be prepared according to the following Scheme (IIIa):

Scheme (IIIa)

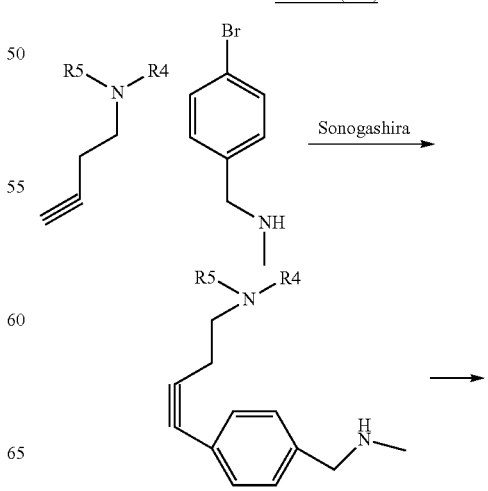

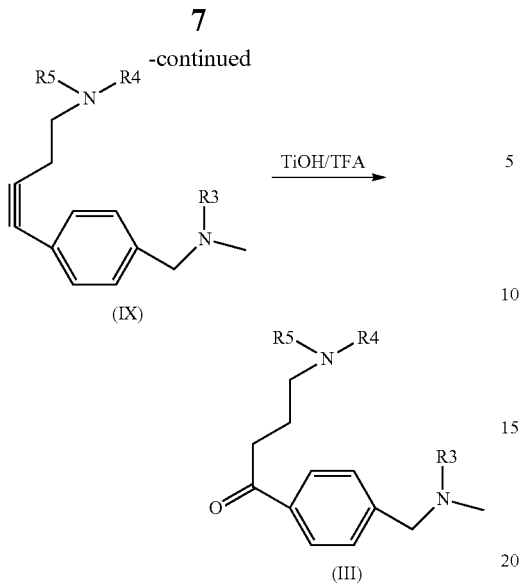

wherein R3, R4 and R5 are as above defined.

Alternatively, compound of formula (III) may be prepared by a Suzuki reaction according to the following Scheme (IIIb) which shows a representative example for the preparation of compound (III) wherein R3 is carboxybenzyl (Cbz) and R4 and R5 forms a phathalimido protecting group:

Compounds of formula (IV) as well as their salts, are also novel compounds and represent a further subject-matter of the present invention.

Compounds of formula (V), provided that R1 is not a hydrogen atom, as well as their salts, are also novel compounds and represent a further subject-matter of the present invention.

Compounds of formula (VI), (VIII) and (IX) as well as their salts, are also novel compounds and represent a further subject-matter of the present invention.

Preferred intermediate compounds according to the present invention are:

compounds of formula (II) wherein R1 is a hydrogen atom or halogen atom, preferably a bromine atom;
compounds of formula (II) wherein R2 is H;
compounds of formula (II) wherein R1 is a hydrogen atom or halogen atom, preferably a bromine atom and R2 is H;
compounds of formula (III) and (IX) wherein R3 is a substituted acyl, preferably a substituted acetyl, more preferably trifluoroacetyl or trichloroacetyl;
compounds of formula (VI) wherein R1 is a hydrogen atom or halogen atom, preferably a bromine atom, R2 is H and R3 is a substituted acyl, preferably a substituted acetyl, more preferably trifluoroacetyl or trichloroacetyl;
compounds of formula (III), (VIII) and (IX) wherein R4 and R5 together with the nitrogen atom to which

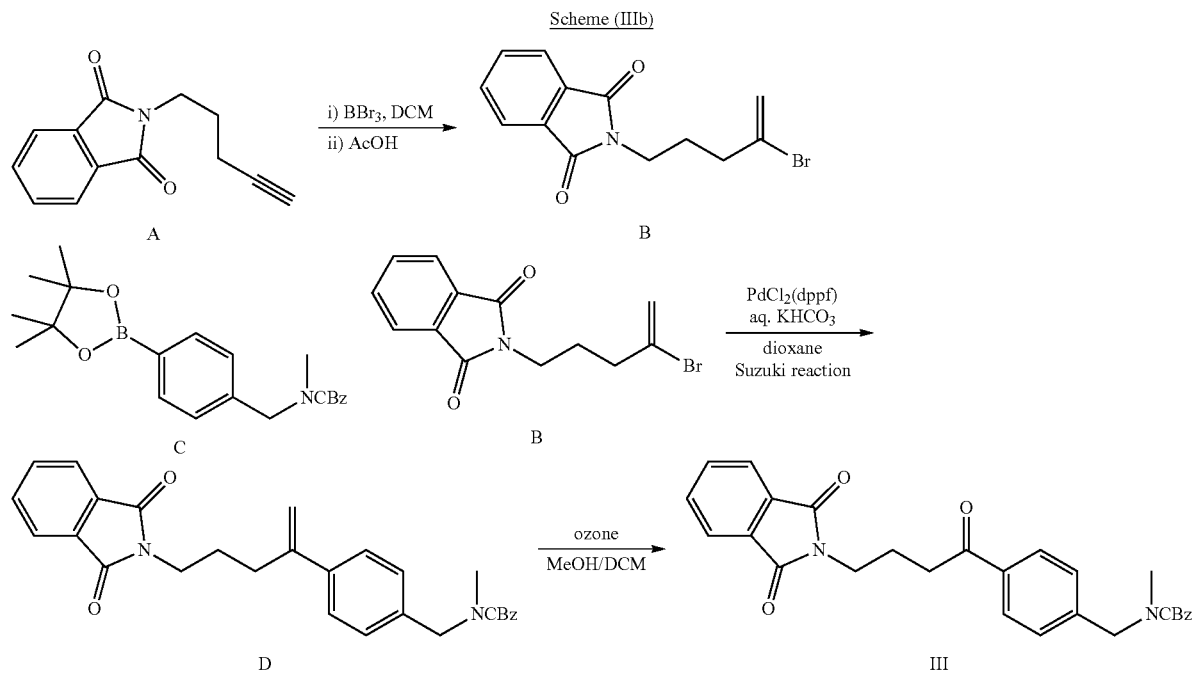

The preparation of compound of formula (III) according to Scheme (IIIa) is preferred according to the invention.

According to a specific embodiment, compound (IX) may also be directly prepared by a one-pot reaction combining the two synthetic steps depicted above.

The compound of formula (III) as well as its salts, is a novel compound and constitutes a further subject-matter of the present invention.

they are bound, form a cyclic protecting group as above defined, preferably a phthalimide group;

compounds of formula (III) and (IX) wherein R3 is a substituted acyl, preferably a substituted acetyl, more preferably trifluoroacetyl or trichloroacetyl and R4 and R5 together with the nitrogen atom to which they are bound, form a cyclic protecting group as above defined, preferably a phthalimide group; as well as their salts.

According to another of its aspects, the invention relates to the use of the novel compounds above and salts thereof as intermediates of synthesis.

According to a preferred embodiment, the invention relates to the use of the novel compounds above as intermediates in the synthesis of rucaparib.

As it is evident from the above Schemes, it can be easily understood that the process of the invention includes approximately seven synthetic steps, which means three to six steps less with respect to the prior art processes. This is an important technical result which is achieved by the invention, especially for an industrial scale production.

According to another of its aspects, the present invention relates to a crystalline form of rucaparib showing the XRPD of FIG. 1 and the peaks indicated in Example 3.

The invention will now be described in more detail by way of examples, for illustrative purposes only.

EXPERIMENTAL SECTION

Definitions
AUC=area under the curve
DCM=dichloromethane
EtOAc=ethyl acetate
EtOH=ethanol
MeOH=methanol
TFA=trifluoroacetic acid
TFAA=trifluoroacetic anhydride
THF=tetrahydrofuran
Materials and Methods Liquid chromatography—mass spectrometry (LCMS) experiments to determine retention times and associated mass ions were performed using one or more of the following Methods A, B, and C:

Method A: Waters BEH (ethylene bridged hybrid) C18 column, 3.0×30 mm, 1.7 μm, was used at a temperature of 50° C. and at a flow rate of 1.5 mL/min, 2 μL injection, mobile phase: (A) water with 0.1% formic acid and 1% acetonitrile, mobile phase; (B) MeOH with 0.1% formic acid; retention time given in minutes.

Method A details: (I) ran on a Binary Pump G1312B, Agilent Technologies, with UV/Vis diode array detector G1315C and Agilent 6130 mass spectrometer in positive and negative ion electrospray mode with UV PDA detection with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B);

Method B: An Agilent Zorbax Bonus RP column, 2.1×50 mm, 3.5 μm, was used at a temperature of 50° C. and at a flow rate of 0.8 mL/min, 2 μL injection, mobile phase: (A) water with 0.1% formic acid and 1% acetonitrile, mobile phase (B) MeOH with 0.1% formic acid; retention time given in minutes.

Method B details: (I) ran on a Binary Pump G1312B, Agilent Technologies, with UV/Vis diode array detector G1315C and Agilent 6130 mass spectrometer in positive and negative ion electrospray mode with UV-detection at 220 and 254 nm with a gradient of 5-95% (B) in a 2.5 min linear gradient (II) hold for 0.5 min at 95% (B)

(III) decrease from 95-5% (B) in a 0.1 min linear gradient (IV) hold for 0.29 min at 5% (B).

Method C: An API 150EX mass spectrometer, Applied Biosystems, linked to a Shimadzu LC-10AT liquid chromatography system, with a diode array detector was used. The spectrometer had an electrospray source operating in positive and negative ion mode. The liquid chromatography was carried out using an Agilent ZORBAX XDB 50×2.1 mm C18 column and a 0.5 mL/minute flow rate. Solvent A: 95% water, 5% acetonitrile containing 0.01% formic acid; Solvent B: acetonitrile. The gradient was shown 0-0.5 min: 2% solvent (B); 0.5-2.5 min: 2% solvent B to 95% solvent (B); 2.5-4.0 min: 95% solvent (B); 4.0-4.2 min: 95% solvent (B) to 2% solvent B; 4.2-6.0 min: 2% solvent (B).

Preparation 1

Preparation of 4-bromo-3-fluoro-5-hydrazineylbenzoic acid hydrochloride

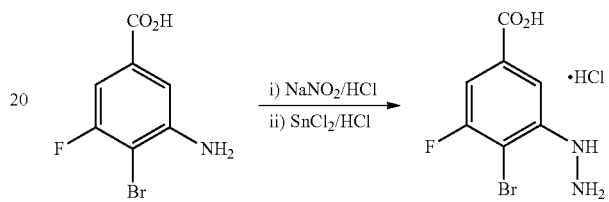

To a cooled (−2° C.) suspension of 3-amino-4-bromo-5-fluorobenzoic acid (5.93 g, 25.3 mmol) in concentrated HCl (100 mL) was added a solution of sodium nitrite (2.10 g, 30.4 mmol) in water (10 mL) at a rate that kept the internal temperature of the reaction below 5° C. The reaction was maintained between 0 and 5° C. for 3 h before cooling to −5° C. A solution of SnCl2 (12.5 g, 65.9 mmol) in concentrated HCl (60 mL) was added at a rate that kept the internal temperature of the reaction below 5° C. After the addition was complete the reaction was allowed to warm to room temperature over 18 h. The reaction was then concentrated under a stream of nitrogen at room temperature for 24 to ~ half of the starting volume. The resultant suspension was cooled to 0° C. and filtered under vacuum on a Buchner funnel for 20 h to give 4-bromo-3-fluoro-5-hydrazineylbenzoic acid hydrochloride (5.77 g).

$^1$H NMR revealed ~2.5 mol % starting aniline in the mixture.

$^1$H NMR (400 MHz, DMSO-d6) δ=8.37 (br. s., 1H), 7.48 (s, 1H), 7.38 (dd, J=1.6, 8.6 Hz, 1H). 19F NMR (376 MHz, DMSO-d6) δ=−105.43 (d, J=7.9 Hz, 1F). LC/MS RT=0.31 min., 249.0 [M+H]$^+$ Preparation 2

Preparation of 2-(4-(4-((methylamino)methyl)phenyl)but-3-yn-1-yl)isoindoline-1,3-dione

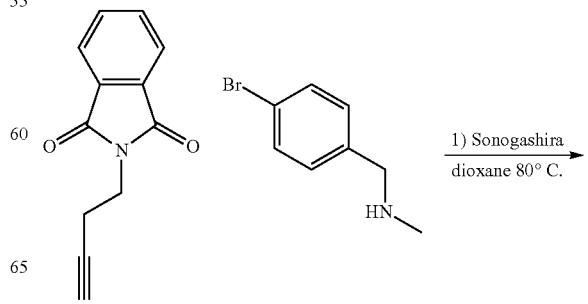

-continued

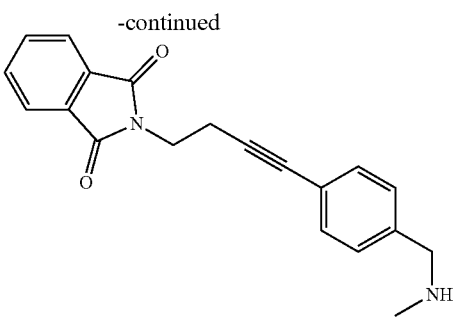

A mixture of 1-(4-bromophenyl)-N-methylmethanamine (14.0 g, 70.0 mmol), 2-(but-3-yn-1-yl)isoindoline-1,3-dione (16.5 g, 83.0 mmol), CuI (3.33 g, 17.5 mmol) and $Cs_2CO_3$ (114 g, 351 mmol) in deoxygenated dioxane (280 mL) was further deoxygenated by bubbling nitrogen gas for 1.25 h. through the mixture. $PdCl_2([1,1'$-bis(diphenylphosphino)ferrocene]) (5.71 g, 7.00 mmol) was added and the mixture further deoxygenated with nitrogen for 1 h before heating to 80° C. for 18 h under an atm. of $N_2$. The reaction was allowed to cool to room temperature and filtered through celite with EtOAc. The organic mother liquor was washed with 1 molar NaOH, water, brine, dried with $Na_2SO_4$, filtered and concentrated in vacuo. The residue was chromatographed on silica gel (330 g Isco column, 1 to 10% MeOH in DCM with 1% $NEt_3$ in the eluents over 36 min.) to give 23.3 g of 2-(4-(4-((methylamino)methyl)phenyl)but-3-yn-1-yl)isoindoline-1,3-dione as a black oil that was 86% 74 by weight. The raw product was used as is in the next reaction.

$^1$H NMR (400 MHz, chloroform-d) δ=7.87 (dd, J=3.0, 5.5 Hz, 2H), 7.73 (dd, J=3.1, 5.4 Hz, 2H), 7.31-7.28 (m, 2H), 7.23-7.19 (m, 2H), 3.97 (t, J=7.1 Hz, 2H), 2.83 (t, J=7.1 Hz, 2H), 2.43 (s, 3H), 1.19 (t, J=7.2 Hz, 2H). LC/MS RT=0.49 min., 319.0 $[M+H]^+$ Preparation 3

Preparation of N-(4-(4-(1,3-dioxoisoindolin-2-yl)but-1-yn-1-yl)benzyl)-2,2,2-trifluoro-N-methylacetamide

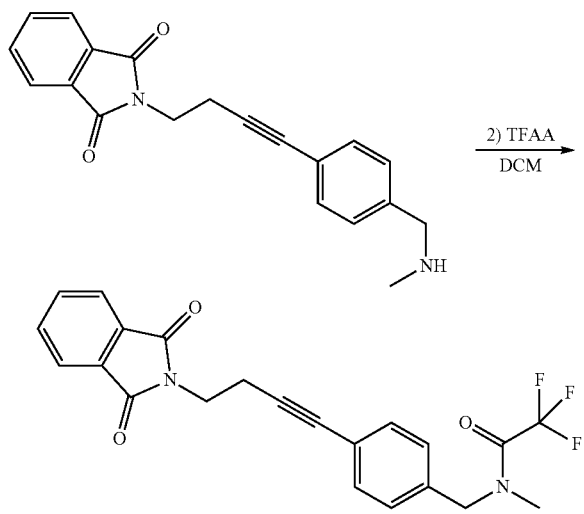

To a cooled (0° C.) solution of 2-(4-(4-((methylamino)methyl)phenyl)but-3-yn-1-yl)isoindoline-1,3-dione (23.3 g, ~86% by weight, 0.0600 mol) and triethylamine (25.1 mL, 0.180 mol) in DCM (300 mL) was added trifluoroacetic anhydride (12.5 mL, 0.0900 mol) dropwise over 13 minutes. The reaction was allowed to slowly warm to room temperature over 18 h before it was quenched into saturated aq $NaHCO_3$. The organic layer was separated and the aq. layer was back extracted 3×DCM. The combined organic layers were washed with brine, dried with $Na_2SO_4$, filtered and concentrated in vacuo to give a black oil. Residue was chromatographed on silica gel (330 g Isco column, 5 to 50% EtOAc in heptanes over 36 min.) to give 15.3 g of N-(4-(4-(1,3-dioxoisoindolin-2-yl)but-1-yn-1-yl)benzyl)-2,2,2-trifluoro-N-methylacetamide as an orange oil that solidified to an off white solid on standing (53% over 2 steps).

$^1$H NMR (400 MHz, chloroform-d) δ=7.88 (dd, J=3.1, 5.4 Hz, 2H), 7.74 (dd, J=3.0, 5.4 Hz, 2H), 7.38-7.31 (m, 2H), 7.18-7.08 (m, 2H), 4.63-4.56 (m, 2H), 4.03-3.93 (m, 2H), 3.03 (s, 2H), 2.90 (s, 1H), 2.86-2.79 (m, 2H).

$^{19}$F NMR (376 MHz, chloroform-d) δ=−68.00 (s, 1F), −69.55 (d, J=1.5 Hz, 2F), −72.57 (s, 1F). LC/MS RT=1.36 min., 415.0 $[M+H]^+$ Preparation 4

Preparation of N-(4-(4-(1,3-dioxoisoindolin-2-yl)butanoyl)benzyl)-2,2,2-trifluoro-N-methylacet amide

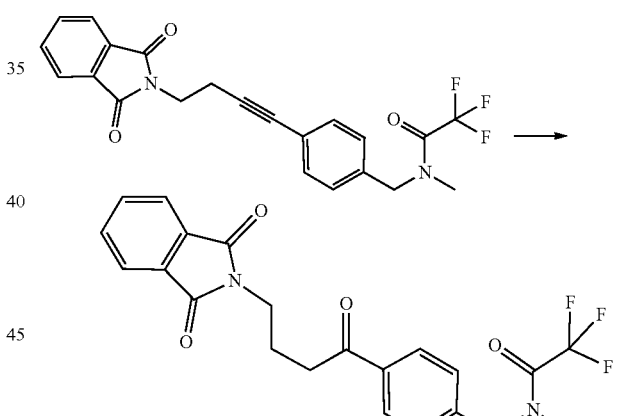

To a solution of N-(4-(4-(1,3-dioxoisoindolin-2-yl)but-1-yn-1-yl)benzyl)-2,2,2-trifluoro-N-methylacetamide (15.3 g, 36.9 mmol) in TFA (111 mL) was added a 3.6:1 solution of triflic acid/water (74 mL). The reaction was allowed to stir at room temperature for 18 h before it was slowly quenched into an aqueous solution of $NaHCO_3$ (300 g in 3.5 L water). The contents were split into two portions and each was extracted 3×0.6 L EtOAc. Glassware used for quench was also washed with EtOAc to dissolve organic oil that had adhered to it. The combined organic fractions were dried with $Na_2SO_4$, filtered and concentrated in vacuo. The residue was chromatographed on silica gel (220 g Isco column, 5 to 100% EtOAc in heptane over 33 min.) to give impure product, which was rechromatographed (220 g Isco column, 5 to 100% EtOAc in heptane over 33 min.) to give 10.6 g of N-(4-(4-(1,3-dioxoisoindolin-2-yl)butanoyl)benzyl)-2,2,2-trifluoro-N-methylacetamide as a white solid (66%).

$^1$H NMR (400 MHz, chloroform-d) δ=7.98-7.90 (m, 2H), 7.88-7.81 (m, 2H), 7.76-7.69 (m, 2H), 7.35-7.27 (m, 2H), 4.69 (s, 2H), 3.83 (t, J=6.8 Hz, 2H), 3.10-3.01 (m, 4H), 2.95 (s, 1H), 2.21-2.11 (m, 2H). $^{19}$F NMR (376 MHz, chloroform-d) δ=−68.14 (s, 1F), −69.57 (d, J=1.3 Hz, 2F). LC/MS RT=1.22 min., 433.0 [M+H]$^+$ Example 1

Preparation of 7-bromo-3-(2-(1,3-dioxoisoindolin-2-yl)ethyl)-6-fluoro-2-(4-((2,2,2-trifluoro-N-methylacetamido)methyl)phenyl)-1H-indole-4-carboxylic acid

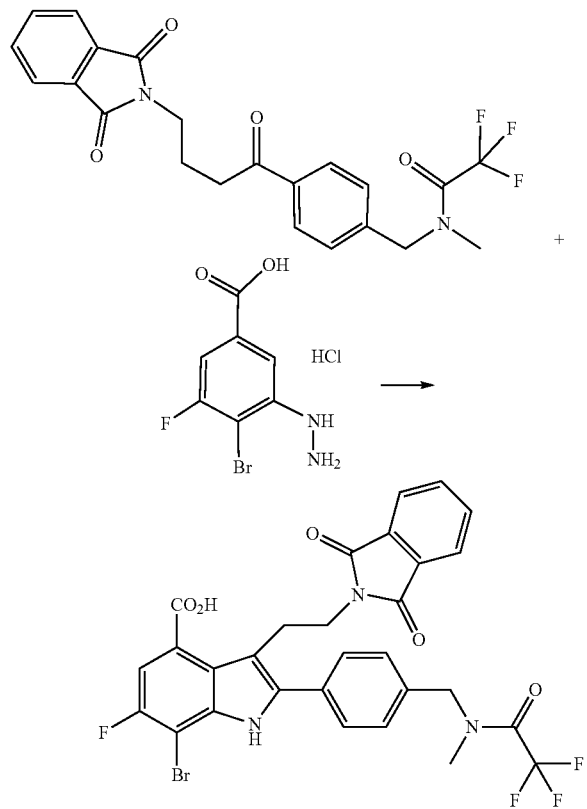

A mixture of N-(4-(4-(1,3-dioxoisoindolin-2-yl)butanoyl)benzyl)-2,2,2-trifluoro-N-methylacetamide (8.71 g, 20.1 mmol) and 4-bromo-3-fluoro-5-hydrazineylbenzoic acid hydrochloride (5.75 g, 20.1 mmol) was diluted in glacial acetic acid (200 mL). Boron trifluoride diethyl etherate (16.4 mL, 133 mmol) was added and the mixture heated to 90° C. under an atm of N$_2$ for 18 h. The mixture dissolved after ~5 min. of heating. The reaction was allowed to cool to room temperature and concentrated in vacuo to give a black tar. The residue was chromatographed on silica gel (330 g Isco column, 0 to 100% EtOAc in heptane over 36 min.) to give 9.84 g of 7-bromo-3-(2-(1,3-dioxoisoindolin-2-yl)ethyl)-6-fluoro-2-(4-((2,2,2-trifluoro-N-methylacetamido)methyl)phenyl)-1H-indole-4-carboxylic acid that was used as is in the next reaction.

LC/MS RT=1.27 min., 645.6 [M−H]$^−$, 79% AUC at 254 nm.

Example 2

Preparation of 9-bromo-8-fluoro-2-{4-[(methylamino)methyl]phenyl}-1,3,4,5-tetrahydro-6H-pyrrolo[4,3,2-ef][2]benzazepin-6-one

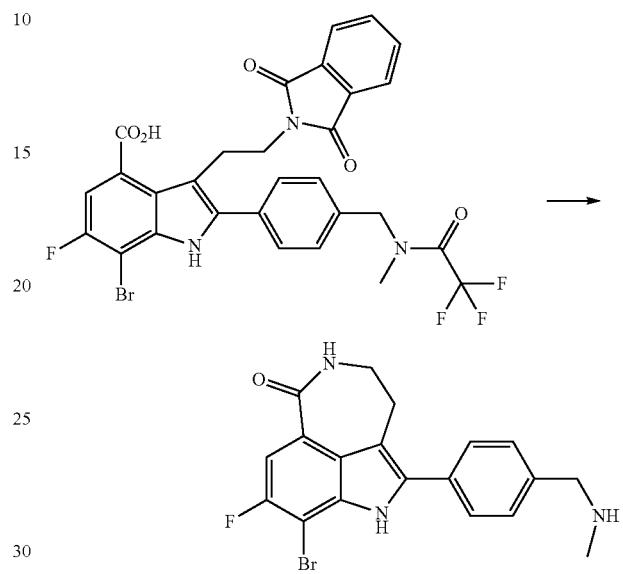

A solution of 7-bromo-3-(2-(1,3-dioxoisoindolin-2-yl)ethyl)-6-fluoro-2-(4-(2,2,2-trifluoro-N-methylacetamido)methyl)phenyl)-1H-indole-4-carboxylic acid (9.84 g, 79% AUC at 254 nm.) and hydrazine (1.70 mL, 54.4 mmol) in 1:1 EtOH/THF (110 mL) was transferred to a 1 L stainless steel pressure reactor and heated under pressure to 110° C. for 9 h. The reaction was allowed to cool to room temperature, transferred to a round bottom flask and concentrated in vacuo. The residue was chromatographed on silica gel (120 g gold Isco column, 0 to 40% MeOH in DCM with 1% NEt$_3$ in the eluents over 35 min.) to give 1.63 g of 7-bromo-8-fluoro-5-(4-((methylamino)methyl)phenyl)-2,3,4,6-tetrahydro-1H-azepino[5,4,3-cd]indol-1-one as a tan solid which was used without further purification. LC/MS RT=1.27 min., 403.8 [M+H]$^+$, 89% AUC at 254 nm.

Example 3

Preparation of Rucaparib

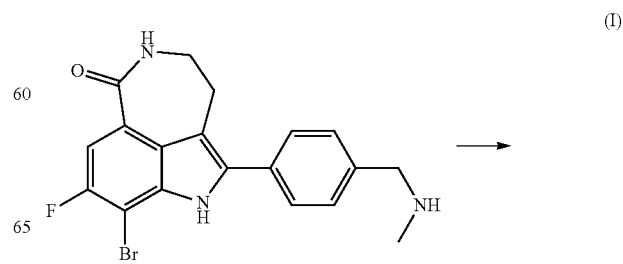

(I)

-continued

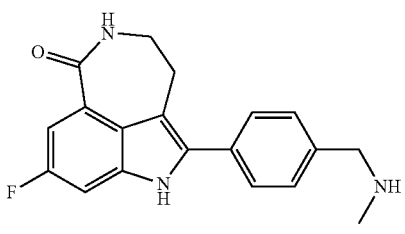

A suspension of 9-bromo-8-fluoro-2-{4-[(methylamino)methyl]phenyl}-1,3,4,5-tetrahydro-6H-pyrrolo[4,3,2-ef][2]benzazepin-6-one (1.61 g, 89% AUC at 254 nm) in MeOH (80 mL) was heated to reflux for ~5 min. until a solution was obtained. Solution was allowed to cool to room temperature over 30 min. before 5% Pd/Carbon (Degussa type E101 NO/W, 800 mg) and concentrated HCl (1.00 mL, 12 mmol) was added. Hydrogen gas (~3-5 L) was bubbled through the reaction before it was allowed to vigorously stir at room temperature under an atmosphere of hydrogen for 18 h. Nitrogen (~3-5 L) was bubbled through the reaction before it was filtered through celite under an inverse funnel of nitrogen. The celite was rinsed with 200 mL of MeOH and $NEt_3$ (7 mL) was added to the mother liquor obtained before it was concentrated in vacuo. The residue (3.6 g) was dissolved in MeOH and split into 3 equal batches that were independently concentrated in vacuo and chromatographed on a C18 reverse phase column (50 g Isco gold column, 5% MeOH in water for 1 min., then 5% to 100% MeOH in water over 12.5 min.) to give 734 mg of rucaparib as an off white solid.

$^1$H NMR (400 MHz, DMSO-$d_6$) δ=11.78 (s, 1H), 8.27 (t, J=5.8 Hz, 1H), 7.71-7.66 (m, 2H), 7.65-7.60 (m, 2H), 7.44 (dd, J=2.4, 11.0 Hz, 1H), 7.35 (dd, J=2.4, 9.1 Hz, 1H), 4.10 (s, 2H), 3.43-3.37 (m, 2H), 3.09-3.02 (m, 2H), 2.54 (s, 3H).

$^{19}$F NMR (376 MHz, DMSO-$d_6$) δ=−120.95 (dd, J=9.2, 10.9 Hz, 1F).

LC/MS RT=0.14 min., 324.2 [M+H]$^+$, 322.2 [M−H]$^-$,

HPLC RT=3.586 min., 96.6218% at 254 nm.

XRPD of rucaparib obtained according to Example 3 is depicted in FIG. 1.

The acquisition data and peak list are as follows:

| Scan Type | Coupled TwoTheta/Theta |
|---|---|
| Scan Mode | Continuous PSD fast |
| Start | 2.000 |
| End | 40.017 |
| Step size | 0.050 |
| Time per Step | 192.00 |
| Anode | Cu |
| Kα1 | 1.54 |
| Generator kV | 40.0 |
| Generator mA | 40.0 |
| PSD Opening | 2.940 |
| Primary Soller slit | 2.500 |
| Secondary Soller slit | 2.500 |
| Sample rotation speed | 15.000 |
| Divergence Slit | 0.600 |
| Antiscatter Slit | 3.000 |
| Slit Mode | Fixed |

Peak List

| Angle | D Value | Net Intensity | Gross Intensity | Rel Intensity |
|---|---|---|---|---|
| 6.907 | 12.78733 | 2405 | 2994 | 21.8% |
| 7.954 | 11.10643 | 2488 | 2946 | 22.5% |
| 11.178 | 7.90909 | 801 | 1176 | 7.3% |
| 11.703 | 7.55534 | 2437 | 2813 | 22.1% |
| 12.205 | 7.24602 | 461 | 838 | 4.2% |
| 12.405 | 7.12970 | 2962 | 3339 | 26.8% |
| 13.804 | 6.41007 | 384 | 764 | 3.5% |
| 14.308 | 6.18523 | 413 | 793 | 3.7% |
| 14.908 | 5.93775 | 2367 | 2748 | 21.4% |
| 15.206 | 5.82210 | 993 | 1375 | 9.0% |
| 15.805 | 5.60252 | 2088 | 2471 | 18.9% |
| 15.952 | 5.55125 | 1662 | 2045 | 15.1% |
| 16.612 | 5.33239 | 1091 | 1474 | 9.9% |
| 16.707 | 5.30219 | 1187 | 1571 | 10.8% |
| 16.957 | 5.22451 | 711 | 1095 | 6.4% |
| 17.160 | 5.16330 | 528 | 912 | 4.8% |
| 17.505 | 5.06216 | 274 | 659 | 2.5% |
| 18.156 | 4.88217 | 1297 | 1682 | 11.7% |
| 18.808 | 4.71427 | 651 | 1037 | 5.9% |
| 19.759 | 4.48962 | 1236 | 1622 | 11.2% |
| 20.461 | 4.33697 | 376 | 762 | 3.4% |
| 21.112 | 4.20486 | 376 | 762 | 3.4% |
| 21.961 | 4.04410 | 1340 | 1726 | 12.1% |
| 22.461 | 3.95521 | 1414 | 1800 | 12.8% |
| 22.809 | 3.89566 | 2464 | 2850 | 22.3% |
| 23.602 | 3.76658 | 771 | 1156 | 7.0% |
| 23.961 | 3.71094 | 1905 | 2290 | 17.3% |
| 24.510 | 3.62892 | 11038 | 11423 | 100.0% |
| 25.218 | 3.52875 | 582 | 966 | 5.3% |
| 25.559 | 3.48243 | 2961 | 3344 | 26.8% |
| 26.013 | 3.42256 | 1032 | 1415 | 9.4% |
| 26.562 | 3.35309 | 872 | 1255 | 7.9% |
| 27.012 | 3.29826 | 1225 | 1606 | 11.1% |
| 27.761 | 3.21095 | 660 | 1040 | 6.0% |
| 28.213 | 3.16058 | 826 | 1206 | 7.5% |
| 28.664 | 3.11182 | 576 | 955 | 5.2% |
| 29.816 | 2.99418 | 566 | 943 | 5.1% |
| 30.564 | 2.92260 | 447 | 822 | 4.1% |
| 32.260 | 2.77270 | 1308 | 1679 | 11.9% |
| 33.865 | 2.64482 | 440 | 806 | 4.0% |
| 35.017 | 2.56043 | 441 | 804 | 4.0% |
| 39.176 | 2.29766 | 271 | 637 | 2.5% |

The invention claimed is:

1. A process for the preparation of of rucaparib of formula (I),

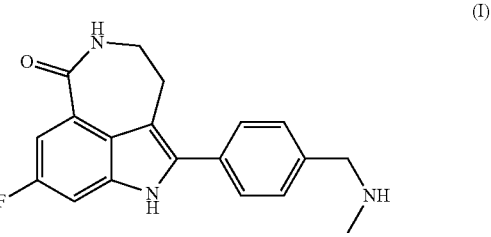

(I)

or a salt thereof, which comprises:
a) reacting a compound of formula (II)

(II)
[structure of compound II: fluoro-substituted benzoate with NH-NH2 and R1 substituents]

wherein
R1 is selected from hydrogen a halogen atom, a cyano group, a sulfonyl group, an —O— sulfonyl group; and
R2 is selected from hydrogen, an alkyl group, an aryl group or an aryl-alkylgroup;
or a salt thereof,
with a compound of formula (III)

(III)
[structure of compound III]

wherein R3 is a protecting group;
R4 is hydrogen or a protecting group; and
R5 is a protecting group;
or R4 and R5, together with the nitrogen atom to which they are bound, form a cyclic protecting group;
to obtain a compound of formula (IV)

(IV)
[structure of compound IV]

b) converting compound (IV) into the corresponding lactam of formula (V)

(V)
[structure of compound V]

c) when R1 is other than a hydrogen atom, removing R1 from the lactam of formula (V) to obtain rucaparib of formula (I);
d) optionally, transforming rucaparib in a salt thereof.

2. The process according to claim 1, wherein the compound of formula (II) is in the form of a salt thereof.

3. The process according to claim 1, wherein R1 is a hydrogen atom or a halogen atom.

4. The process according to claim 3, wherein R1 is a bromine atom.

5. The process according claim 1, wherein R2 is a hydrogen atom.

6. The process according to claim 1, wherein R3 is selected from a trifluoroacetyl and a trichloroacetyl group.

7. The process according to claim 6, wherein R3 is selected from a trifluoroacetyl and a trichloroacetyl group.

8. The process according to claim 1, wherein R4 and R5 together with the nitrogen atom to which they are bound, form a cyclic protecting group.

9. The process according to claim 8, wherein R4 and R5 together with the nitrogen atom to which they are bound, form a phthalimide group.

10. The process according to claim 1, wherein R4 and R5 are removed from compound (IV) before step b) to provide compound of formula (VI)

(VI)
[structure of compound VI]

or a salt thereof.

11. The process according to claim 10, wherein R1 is a hydrogen atom or a halogen atom, R2 is selected from hydrogen, an alkyl group, an aryl group or an aryl-alkylgroup; or a salt thereof,
and wherein R3 is a protecting group.

12. A compound selected from a compound of formula (II)

[chemical structure of formula (II)]

wherein R1 is selected from hydrogen a halogen atom, a cyano group, a sulfonyl group, an —O-sulfonyl group; and
R2 is selected from hydrogen, an alkyl group, an aryl group or an aryl-alkylgroup;
or a salt thereof;
a compound of formula (III)

[chemical structure of formula (III)]

wherein R3 is a protecting group;
R4 is hydrogen or a protecting group; and
R5 is a protecting group;
or R4 and R5, together with the nitrogen atom to which they are bound, form a cyclic protecting group;
a compound of formula (IV)

[chemical structure of formula (IV)]

a compound of formula (V)

[chemical structure of formula (V)]

a compound of formula (VI)

[chemical structure of formula (VI)]

a compound of formula (VIII)

[chemical structure of formula (VIII)]

and
a compound of formula (IX)

[chemical structure of formula (IX)]

provided that R1 is not a hydrogen atom in compound of formula (V), as well as their salts.

13. Crystalline form of rucaparib showing the XRPD:

| Angle | D Value | Net Intensity | Gross Intensity | Rel Intensity |
|---|---|---|---|---|
| 6.907 | 12.78733 | 2405 | 2994 | 21.8% |
| 7.954 | 11.10643 | 2488 | 2946 | 22.5% |
| 11.178 | 7.90909 | 801 | 1176 | 7.3% |
| 11.703 | 7.55534 | 2437 | 2813 | 22.1% |

-continued

| Angle | D Value | Net Intensity | Gross Intensity | Rel Intensity |
|---|---|---|---|---|
| 12.205 | 7.24602 | 461 | 838 | 4.2% |
| 12.405 | 7.12970 | 2962 | 3339 | 26.8% |
| 13.804 | 6.41007 | 384 | 764 | 3.5% |
| 14.308 | 6.18523 | 413 | 793 | 3.7% |
| 14.908 | 5.93775 | 2367 | 2748 | 21.4% |
| 15.206 | 5.82210 | 993 | 1375 | 9.0% |
| 15.805 | 5.60252 | 2088 | 2471 | 18.9% |
| 15.952 | 5.55125 | 1662 | 2045 | 15.1% |
| 16.612 | 5.33239 | 1091 | 1474 | 9.9% |
| 16.707 | 5.30219 | 1187 | 1571 | 10.8% |
| 16.957 | 5.22451 | 711 | 1095 | 6.4% |
| 17.160 | 5.16330 | 528 | 912 | 4.8% |
| 17.505 | 5.06216 | 274 | 659 | 2.5% |
| 18.156 | 4.88217 | 1297 | 1682 | 11.7% |
| 18.808 | 4.71427 | 651 | 1037 | 5.9% |
| 19.759 | 4.48962 | 1236 | 1622 | 11.2% |
| 20.461 | 4.33697 | 376 | 762 | 3.4% |
| 21.112 | 4.20486 | 376 | 762 | 3.4% |
| 21.961 | 4.04410 | 1340 | 1726 | 12.1% |
| 22.461 | 3.95521 | 1414 | 1800 | 12.8% |

-continued

| Angle | D Value | Net Intensity | Gross Intensity | Rel Intensity |
|---|---|---|---|---|
| 22.809 | 3.89566 | 2464 | 2850 | 22.3% |
| 23.602 | 3.76658 | 771 | 1156 | 7.0% |
| 23.961 | 3.71094 | 1905 | 2290 | 17.3% |
| 24.510 | 3.62892 | 11038 | 11423 | 100.0% |
| 25.218 | 3.52875 | 582 | 966 | 5.3% |
| 25.559 | 3.48243 | 2961 | 3344 | 26.8% |
| 26.013 | 3.42256 | 1032 | 1415 | 9.4% |
| 26.562 | 3.35309 | 872 | 1255 | 7.9% |
| 27.012 | 3.29826 | 1225 | 1606 | 11.1% |
| 27.761 | 3.21095 | 660 | 1040 | 6.0% |
| 28.213 | 3.16058 | 826 | 1206 | 7.5% |
| 28.664 | 3.11182 | 576 | 955 | 5.2% |
| 29.816 | 2.99418 | 566 | 943 | 5.1 % |
| 30.564 | 2.92260 | 447 | 822 | 4.1 % |
| 32.260 | 2.77270 | 1308 | 1679 | 11.9% |
| 33.865 | 2.64482 | 440 | 806 | 4.0% |
| 35.017 | 2.56043 | 441 | 804 | 4.0% |
| 39.176 | 2.29766 | 271 | 637 | 2.5%. |

\* \* \* \* \*